US006432358B2

(12) United States Patent
Norris et al.

(10) Patent No.: US 6,432,358 B2
(45) Date of Patent: Aug. 13, 2002

(54) DIAGNOSTIC ASSAY DEVICE

(75) Inventors: Philip R. Norris, North Reading, MA (US); Peter H. Roth, Quechee, VT (US); Robert J. Wadja, Wellesley, MA (US)

(73) Assignee: Polaroid Corporation, Cambridge, MA (US)

( * ) Notice: Subject to any disclaimer, the term of this patent is extended or adjusted under 35 U.S.C. 154(b) by 0 days.

(21) Appl. No.: 09/238,970

(22) Filed: Jan. 27, 1999

(51) Int. Cl.[7] ................................................ G01N 33/48

(52) U.S. Cl. ........................... 422/58; 422/61; 436/165; 436/169

(58) Field of Search ............................. 422/56, 58, 61; 436/164–166, 169–170, 808

(56) References Cited

U.S. PATENT DOCUMENTS

| | | | | | |
|---|---|---|---|---|---|
| 3,415,361 | A | | 12/1968 | Adams, Jr. et al. | 206/47 |
| 3,713,779 | A | * | 1/1973 | Sirago et al. | 422/58 |
| 3,865,548 | A | | 2/1975 | Padawer | 23/230 R |
| 4,246,339 | A | * | 1/1981 | Cole et al. | 422/101 |
| 4,264,560 | A | | 4/1981 | Natelson | 422/58 |
| 4,510,393 | A | | 4/1985 | Sell et al. | 250/475.2 |
| 4,587,221 | A | | 5/1986 | Cais et al. | 436/560 |
| 4,797,259 | A | | 1/1989 | Matkovich et al. | 422/101 |
| 5,035,866 | A | | 7/1991 | Wannlund | 422/102 |
| 5,104,812 | A | * | 4/1992 | Kurn et al. | 422/58 |
| 5,106,758 | A | * | 4/1992 | Adler et al. | 436/165 |
| 5,418,171 | A | | 5/1995 | Kimura et al. | 436/518 |
| 5,552,276 | A | | 9/1996 | Mochida et al. | 435/6 |

* cited by examiner

*Primary Examiner*—Lyle A. Alexander

(57) ABSTRACT

A diagnostic device adapted to retain a fluid sample to be analyzed until it is desired to initiate the analytical test is described. The device includes a deformable material layer, a well for holding a fluid sample, a porous material and a diagnostic assay element.

8 Claims, 2 Drawing Sheets

DIAGNOSTIC ASSAY DEVICE

This application is directed to a diagnostic assay device and, more particularly, to a diagnostic assay device which allows retention of a fluid test sample applied to the assay device until it is desired to carry out its interaction with the test materials utilized to provide a detectable change.

BACKGROUND OF THE INVENTION

Devices for use in diagnostic assays are known in the art, including devices which provide a luminescence readout signal as an indication of whether a particular analyte or metabolite is present in a test fluid. U.S. Pat. No. 3,390,962 discloses a biochemical test plate for the facile determination of the immunoprecipitation titer of an antigen-antibody reaction and for determining the antigenic similarities between several antigens when each is at its optimum concentration for the precipitin reaction. In operation, a constant concentration of antibody is disposed in troughs and serially diluted serum or antigen is placed individually into the cup-shaped depressions of the apertures, thereby measuring the immunodiffusion precipitin reaction over a concentration range.

U.S. Pat. No. 3,415,361 discloses a disposable test device and container therefor. The test device described therein includes a container in which pre-measured quantities of reactants for a chemical or immunological test are stored ready for use, with the container being adapted to provide a reaction vessel for the test and to permit observation of visible changes indicating the occurrence of and/or the extent of the reaction caused by the introduction thereinto of an aliquot sample of fluid to be tested, whereby tests can be carried out with a minimum of manipulative steps and supportive equipment.

U.S. Pat. No. 3,865,548 discloses an analytical apparatus for performing chemical analysis and, in particular, to small load operation biomedical test needs. The apparatus described therein comprises a cuvette having therein a first porous barrier which serves to compartmentalize the cuvette, and a first test reagent fluid in a first reagent compartment in the cuvette, the barrier being in direct contact therewith, a second porous barrier and a second test reagent fluid being present, the second test reagent being disposed in a second compartment on the side of the second barrier away from the first reagent compartment, the second barrier being in direct contact with the second test reagents.

U.S. Pat. No. 4,264,560 discloses a clinical analytical system which includes an arrangement for the chemical analysis of a small quantity of sample wherein a specimen of small size is passed through a porous distribution first medium onto a reagent-containing second medium. The reagent-containing second medium is a thin, flat, liquid-impervious medium. A reagent is encapsulated upon the second medium as a flat, liquid-phase surface. The first and second mediums are so arranged and disposed that when firmly pressed together, the encapsulated liquid reagent will be liberated and the specimen will be distributed through the first medium onto the liquid-phase liberated reagent where the subsequent reaction of the liquid-phase reagent and the specimen can then be identified by reading means.

U.S. Pat. No. 4,510,393 discloses a self-contained, portable photo chamber for photographically recording the extent of a chemical reaction such as in an immunological test, wherein a substrate emitting radiation such as gamma radiation is supported in facing contact with a film and with intensifying means, so that exposure time is reduced as a result of emission of further radiation such as a visible light from the intensifying means and its recording on the film.

U.S. Pat. No. 4,587,221 discloses a non-centrifugation/non-decantation method for carrying out specific binding assay tests, wherein liquid and solid phases are present. The device described therein consists of a mixing reservoir into which is fitted snugly a mixing separator having a channel in the vertical axis of the mixer separator. A rack holding a number of the mixing reservoirs containing the incubated reagents and analytes, capped with the mixer separators, is placed into a press-device designed to perform at a controlled rate a downward movement. The mixer separators are pushed downwards into the mixing reservoirs at a chosen rate for a preselected distance to complete the mass transport and separation operations. The separation devices are removed and either one of the separated phases can be measured in the desired analytical instrument for a quantitative or qualitative determination.

U.S. Pat. No. 4,797,259 discloses a diagnostic test device which includes a plate having at least one well, preferably a plurality of wells, each with an open bottom across which a composite membrane comprising three layers is placed, with a hydrophobic, liquid-tight seal provided at the periphery of the each well. The composite membrane from the top of the upstream side to the bottom or downstream side, in sequence, includes a first reaction or filtration layer formed from a thin, lipophilic, microporous membrane, a second or sealing layer, preferably a hydrophobic material in sheet or fiber form, such as nonwoven polypropylene fibers, and a liquophobic, preferably hydrophobic, barrier layer having one or more apertures which allows liquid to exit the well while eliminating lateral migration of a pendant liquid drop. The liquophobic seal provided by the liquophobic sealing layer eliminates “cross-talk” by lateral diffusion or wicking.

U.S. Pat. No. 5,035,866 discloses an apparatus for performing and measuring chemical reactions which includes a reaction test apparatus having reaction wells wherein reactants are controllably mixed, and exposure apparatus which receives and positions the reaction test apparatus adjacent a photographic film. Each of the reaction wells includes at least two reaction cups, arranged one above the other. The uppermost reaction cups have orifices in the bottoms, so that the liquid can be mixed and reacted in the uppermost cup, and then controllably transferred to the lower cup to be mixed with additional reactants. In a preferred embodiment, the reaction cups are supported in plates that are structurally integral with the cups, and are superimposed to make a test block. The test block is retained in the exposure apparatus, and liquid is forced from the upper cup to the lower cup by application of pressure to the top of the upper cup.

U.S. Pat. No. 5,418,171 discloses an apparatus for determining the presence or absence of a target analyte in a liquid sample, which comprises: a container capable of accommodating the liquid sample and having a transparent portion; and an insertion member which is capable of being inserted into the container and which comprises: a porous member which has a main surface and a reverse surface and which has on the main surface a substance capable of specifically binding to the target analyte; and an absorbent bonded to the reverse surface of the porous member; the porous member being supported in the insertion member whereby, when the insertion member is inserted into the container, the main surface can be observed from the outside of the container through the transparent portion of the vessel and the liquid sample is absorbed into the absorbent through the porous member.

U.S. Pat. No. 5,552,276 discloses a measuring apparatus for use in a binding assay to determine the presence or amount of an analyte in a fluid test sample through the use of a label capable of producing a detectable response, which comprises: a porous body having releasably attached thereto an agent soluble in the test sample; a liquid permeable porous reaction membrane disposed below the porous body having defined thereon at least one reaction area, the reaction area having immobilized thereon an affinity substance capable of directly or indirectly capturing the analyte or an agent soluble in the test sample to thereby produce the detectable response; an absorption member disposed below the liquid permeable porous membrane having an opening being positioned below the reaction area of the liquid permeable porous membrane to define a reaction solution storing space within the opening, the absorption member being, arranged so as to contact only a peripheral area of the liquid permeable porous membrane via an intervening liquid impermeable sheet; a liquid impermeable transparent cover disposed below the opening of the absorption member; and a liquid impermeable case accommodating the members and having a top surface adjacent the porous body and a bottom surface adjacent the transparent cover, the top surface having defined therein a top opening for introducing the fluid test sample, and the bottom surface having defined therein a bottom opening for observation of the detectable response.

The design and performance of such prior art diagnostic test elements, kits and processes in some settings is not completely satisfactory. For example, some of the known devices are very complicated, nonportable, systems which require a skilled operator to conduct the analyses. It would be desirable to have a diagnostic device which is capable of either manual use or usable with an apparatus having programmed instructions, which is portable and disposable, and which allows any user to conduct the test.

It would also be desirable to have a device which may be used at home and which enables the user, especially in the case of an elderly or physically-challenged person, to easily load a test sample into a diagnostic test element and to conduct a test to determine the presence of any particular target substance of interest and which, at the same time, provides a device which is relatively inexpensive and which is sturdy, safe and portable.

As the state of the art for diagnostic test elements and kits containing such novel elements continues to move forward, new techniques and materials continue to be developed by those of skill in the art in order to meet the performance criteria required of such diagnostic test elements devices and materials thereof, including the ease of home use, and the reliability and accuracy of the results provided therefrom.

SUMMARY OF THE INVENTION

These and other objects and advantages are obtained in accordance with the invention by providing a diagnostic assay device which includes a layer of a deformable material, a well for holding a fluid sample, a layer of a porous material and a diagnostic assay element spaced apart from the deformable material layer. The porous material forms the bottom surface of the fluid-holding well and is capable of preventing the fluid sample from passing through when the porous material is spaced apart from and out of contact with the diagnostic assay element.

In operation the fluid sample is deposited in the fluid-holding well and retained therein until it is desired to initiate the assay. To initiate the assay, the deformable material layer is deformed so as to bring at least a part of the porous material in contact with the diagnostic assay element whereby at least a portion of the fluid sample is caused to be delivered to the assay element. The assay element includes the reagent(s) necessary to carry out the analysis for the analyte or metabolite of interest. The presence of the analyte or metabolite of interest causes a detectable change to occur within the assay element. The detectable change developed within the assay element may be any of many known types utilized in analytical elements including colorimetric, fluorescent, chemiluminescent etc. Where the signal is fluorescent or chemiluminescent it may be captured by any of a variety of techniques including by exposing a photographic film material, which may be a self-developing photographic film, reading the signal generated with an optical readout system, etc. The detectable change, whether it is a color change which is to be evaluated visually or read spectrophotometrically or whether it is some other type of change such as the generation of a fluorescent or chemiluminescent output signal which is to be read out spectrofluorometrically or captured on a photographic film material or in a luminometer, will be analyzed over a specific portion of the assay element surface, typically a circular or rectangular area substantially in the center of the assay element. Thus, a generally uniform distribution of the fluid sample is provided throughout the area of the assay element which will be analyzed. The assay element may provide a qualitative or a quantitative result.

In a particularly preferred embodiment the diagnostic assay element incorporated in the assay device is a relatively thin film multilayer assay element. The assay device is particularly well suited for use with thin film multilayer diagnostic assay elements because these require only a relatively small volume of test fluid and the assay device is adapted to deliver to the assay element a volume of test fluid which matches the requirements of the assay element.

Deformation of the deformable material layer to initiate the assay can be carried out manually such as by the user applying a downward force to the deformable material layer or the assay device may be inserted into a holding apparatus which can be manipulated to cause the fluid sample to be delivered to the assay element to initiate the assay.

BRIEF DESCRIPTION OF THE DRAWINGS

For a better understanding of the analytical diagnostic device of the invention as well as other objects and further features thereof, reference is made to the following detailed description of various preferred embodiments thereof taken in conjunction with the accompanying drawings wherein.

DESCRIPTION OF THE PREFERRED EMBODIMENTS

Figure 1:
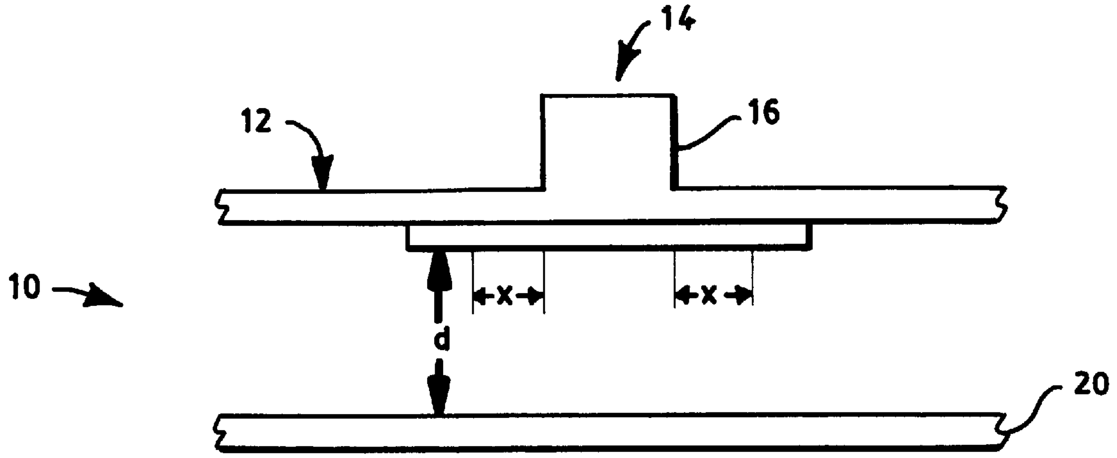
FIG. 1 is a partially-schematic cross-sectional view of an analytical diagnostic device according to the invention.

Referring now to FIG. 1 there is seen a preferred embodiment of an analytical diagnostic device according to the invention. It should be noted that the thickness of the device has been magnified for ease of illustration; the actual preferred devices are relatively thin having a typical total thickness in the range of from about 2.5 mm (0.1 inch) to about 9 mm (0.35 inch). The assay device 10 includes a layer of a deformable material 12 which may be of any suitable material which can be deformed by an applied force. Thermoplastic polymeric materials such as polyethylene, polystyrene, etc. are preferred A particularly preferred material is an approximately 0.5 mm (0.020 inch) thick polystyrene layer. The device 10 further includes a reservoir 14 for holding a fluid sample 15. The reservoir 14, in this illustrative embodiment includes a concentric wall 16 which can be provided as a composite unit with layer 10 such as by injection molding a polymeric material. Of course, it will be apparent that the wall(s) of the reservoir may be of any shape. The reservoir may be configured to hold any required volume of test fluid and therefore the parameters, i.e., the height and diameter or width of the reservoir wall(s) can vary over the required range. In the embodiment of the assay device 10 where the assay element 20 is a thin film multilayer assay element the capacity of the reservoir is typically from about 65 to about 150 $\mu$l and preferably about 125 $\mu$l.

A layer of porous material 18 is adhered to the bottom surface of the deformable material layer 12 in a manner such that it forms the bottom wall of the reservoir 14. The porous material may be of any suitable material which will hold a test fluid in the reservoir until it is desired to initiate the analysis of the fluid. The ability of the porous material to accomplish its function can be provided by one or more properties of the material including its hydrophobicity and pore size. Additionally, the assay element 20 and the layer of porous material should be spaced apart a sufficient distance, d, such that in the event any fluid may form a bead which protrudes from the bottom surface of the porous material, it will not contact the assay element 20 until a force is applied to the deformable material layer 12. The distance, d, is preferably approximately 1 mm.

Although the primary function of the porous material is to retain the fluid sample until the assay test is initiated, the material may be employed to provide other functions. For example, the porous material can provide a molecular sieving function based on the selection of specific properties of the porous material in relation to the properties and/or constituents of the sample fluid and the material to be sieved. For example, the porous material can be coated with a specific material which will bind selectively to a constituent in the test fluid sample thus performing a selective separation, or sieving, function and removing the constituent from the fluid prior to the fluid being deposited on the assay element. In another embodiment one or more materials which are to take part in the test assay can be coated on the porous material and allowed to interact or react with the fluid test sample while it is resident in the reservoir. A colored material such as a dye can be incorporated in the porous material so as to verify that the sample fluid has passed through the column when the assay test is initiated.

Many types of materials are suitable for use in layer 18. Typical suitable materials include membrane materials such as cellulosic membranes and polymeric filter materials of varying pore sizes, poromeric materials such as finely-perforated sheets of polymeric materials, metals, etc. and mesh materials, which may be woven and which may be of polymeric materials such as polyethylene, polypropylene, polyethylene terephthalate and the like. The mesh materials are preferred since these typically provide a more rapid passage of the fluid to the assay element upon initiation of the assay.

Suitable mesh materials include Medifab 07-150/41, a monofilament polyethylene terephthalate material available from Rhone-Poulenc Filtec SA which is approximately 140 mm thick and has a 1:1 weave pattern, an open area of about 40%, a mesh opening of about 150 mm and a mesh count of about 4.3/mm; and Saatifil® polyester 185/41, available from SaatiTech, Inc. which is approximately 179 mm thick and has an open area of about 41%, a mesh opening of about 186 mm, and a mesh count of about 3.4/mm. As mentioned previously, the deformable layer 12 and well 14 are preferably formed as a composite unit by injection molding. The porous material layer 18 may also be attached to deformable layer 12 during the molding process. The polyester mesh materials are preferred because of their heat resistant properties which allow the mesh to be affixed to the deformable layer 12 during the molding operation without significantly adversely affecting the mesh material and to provide the preferred horizontal orientation for layer 18.

As mentioned previously, the porous layer 18 is adhered to the bottom surface of deformable layer 12. It is only necessary to adhere enough of the porous material 18 to maintain it in contact with layer 12 and to prevent the sample fluid from escaping laterally from the reservoir while it is spaced apart from assay element 20. To ensure that the sample fluid does not escape from the reservoir in this manner it is preferred to impregnate with hydrophobic material at least a portion of the porous material which is in contact with layer 12, for example the area indicated by "x" in FIG. 1. Typically, x is from about 0.25 to about 0.75 mm.

In operation, a force is applied to the deformable material layer 12 sufficient to cause the area of the porous material directly below the fluid column to contact the assay element 20 and allow the desired volume of fluid sample to be transferred to the assay element for initiation of the analysis. The fluid sample may comprise any biological fluid such as, for example, saliva, plasma, serum, etc. In the preferred embodiment illustrated in FIG. 1 wherein the assay element 20 is contacted directly by porous material 18 when the deformable layer 12 is deformed, the contact time must be sufficient to allow the required fluid sample volume to be transferred to the assay element, typically up to about five seconds. Of course, the respective materials may be maintained in contact during the time the analysis is being carried out by the assay element.

Although the assay device of the invention has been illustrated in detail with respect to a preferred embodiment wherein the test fluid sample is provided to the assay element by bringing the porous material 1l directly into contact with the assay element, according to other preferred embodiments the porous material and the assay element do not directly contact each other. For example, the assay device may include a fluid delivery system comprised of one or more channels, or grooves, arranged in a layer to provide a lateral liquid flow path which is in fluid communication with one or more assay elements arranged so as to receive the required volume of test fluid. Thus, in a preferred embodiment a plurality of analyses can be carried out for different analytes or metabolites in the same fluid sample. There are disclosed in the art various fluid delivery systems which are suitable for the purpose. See, for example, U.S. Pat. No. 4,906,439 which describes a fluid delivery element for providing a lateral flow of a fluid sample to an assay element. Thus, in a preferred embodiment, the porous material can be brought into contact with a fluid delivery element and the sample fluid delivered to one or more assay elements by lateral flow.

The diagnostic assay element 20 may comprise any diagnostic assay element. Preferred assay elements for incorporation in the assay device of the invention are the thin film assay elements including single layer or multilayer. A typical thin film assay element has a thickness of about 0.1 mm and comprises one or more reagents or reagent layers residing on a support layer which can be transparent or opaque. The assay element may include various other layers as are known in the art including, for example, a light-blocking layer to permit the signal-generating species to be read out without interference from materials present in another layer, a registration layer for holding a signal-generating species form in, or released from, another layer, etc. A preferred multilayer assay element 20 is the type described in U.S. Pat. No. 4,446,232.

The assay element may also include as the uppermost layer, a layer of a material which will assist in spreading the sample fluid substantially uniformly across the surface of the element so as to provide a generally uniform distribution of fluid to the area of the assay element which will be analyzed. Materials which can perform the spreading function are well known in the art. See, for example, U.S. Pat. No. 3,992,158.

Briefly, the multilayer assay element described in U.S. Pat. No. 4,446,232 includes a top layer which includes a labeled member of an antigen-antibody binding pair. Where the analyte or metabolite of interest is an antigen the layer will contain an antibody labeled with a signal-producing moiety such as a fluorescent or chemiluminescent moiety. As the sample fluid diffuses through the layer antigen in the sample fluid will bend to the labeled conjugate. Next the fluid enters a trapping layer which includes material which is the same as the analyte or metabolite which is present in the sample fluid or a material capable of binding the labeled conjugate present in the top layer. An unreacted labeled conjugate from the top layer is bound by the capture material in the trapping layer whereas the antigen-labeled antibody complex is allowed to pass through the trapping layer and enter a signal layer where the complex is anchored.

The labeled conjugate may be detected by means of an optical readout system in which case a light-blocking layer is arranged between the trapping layer and the signal layer or the signal layer may include a material which will interact or react with the label moiety of the labeled conjugate to provide a signal. In either case, the emitted readout signal can be captured by a photographic film such as a self-developing film or by an electronic sensor and quantified.

The force applied to deform layer 12 to initiate the assay can be supplied manually such as by the user pressing down on the layer or the assay device may be incorporated into an apparatus designed for that purpose and the apparatus manipulated to provide the required force. An apparatus suitable for this purpose is disclosed and claimed in copending, commonly-assigned U.S. patent application Ser. No. 9/238,212, filed on even date herewith.

Figure 2:
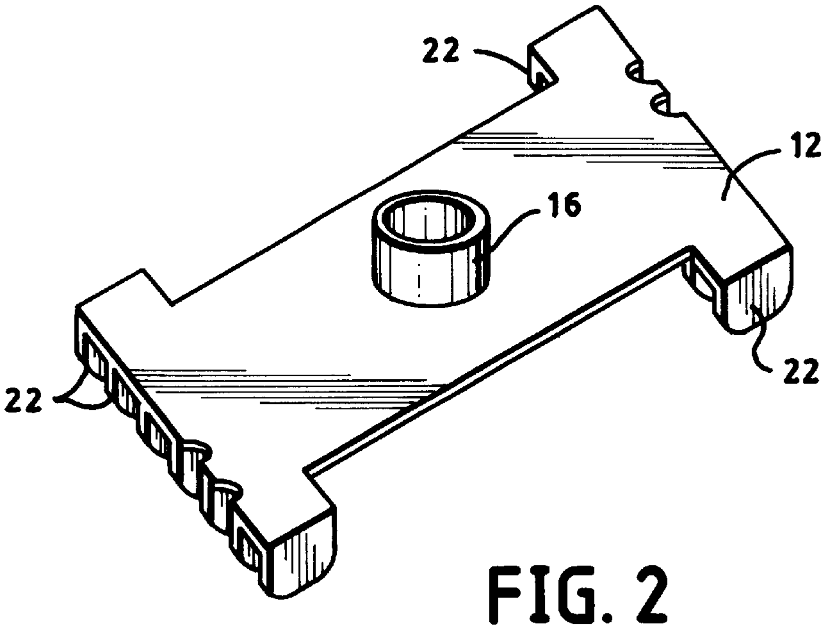
FIG. 2 is a partially schematic, perspective view of an embodiment of the layer of deformable material of the analytical diagnostic device.
Figure 3:
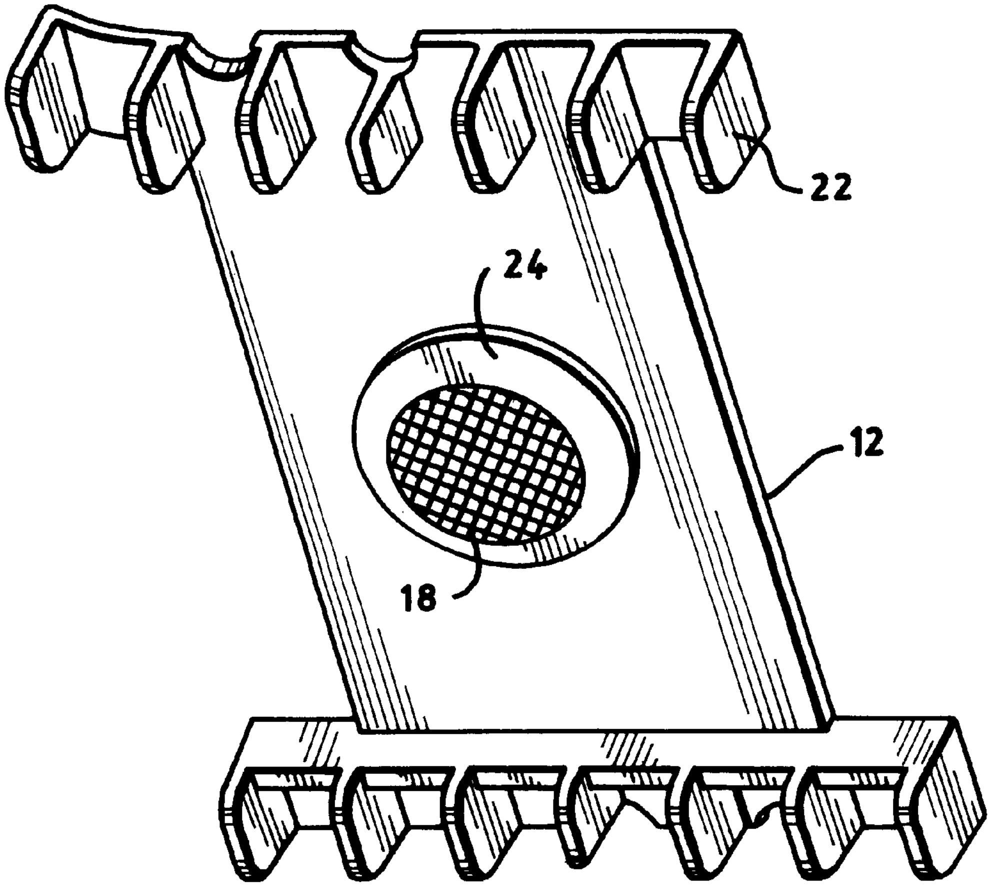
FIG. 3 is a partially-schematic view of the bottom surface of an embodiment of the layer of deformable material of the analytical diagnostic device.

The deformable layer 12 and the assay element 20 may be maintained in spaced-apart relationship by any of many various techniques. In one embodiment the respective layers may be maintained in such relationship by arranging them in a frame. In another embodiment, as illustrated in FIGS. 2 and 3 the spacing may be provided by spacing members 22 which are provided as integral parts of deformable layer 12. FIG. 3 illustrates an embodiment wherein the porous material 18 is surrounded and maintained in place by a ring 24 of the same material which comprises layer 12 and which can be provided conveniently during an injection molding manufacturing procedure. Where the diagnostic device includes a fluid delivery element as described herein, the deformable layer and the fluid delivery element may be maintained apart from each other by similar techniques.

Although the invention has been described with respect to various preferred embodiments thereof, it is not intended to be limited thereto but rather those skilled in the art will recognize that variations and modifications may be made therein which are with the spirit of the invention and the scope of the appended claims.

What is claimed is:

1. A diagnostic device comprising (a) a deformable layer having a first surface and a second surface and having an orifice extending from said first surface through said second surface;

(b) a well extending from said first surface for holding a fluid sample, said well arranged circumferentially about said orifice and having a bottom surface;

(c) a layer of a porous material adhered to said second surface and a part of said layer of porous material forming said bottom surface of said well;

(d) at least one diagnostic element spaced apart from said deformable layer, said deformable layer being capable of being deformed a distance; and (e) whereby said well retains substantially all of the fluid sample and releases the same after an outside force is applied against said deformable layer sufficent to cause said layer of porous material to contact said diagnostic element and allow the fluid sample to be transferred to said diagnostic element for initiation of the analysis.

2. A diagnostic device as defined in claim 1 and further including spacing means for spacing apart said deformable material layer and said diagnostic element.

3. A diagnostic device as defined in claim 2 wherein said spacing means are attached to said deformable material layer.

4. A diagnostic device as defined in claim 1 wherein said well has an annular shape.

5. A diagnostic device as defined in claim 1 wherein said deformable layer is capable of being deformed a distance whereby at least part of said porous material is brought into contact with said diagnostic element.

6. A diagnostic device as defined in claim 1 further including a fluid delivery means in fluid communication with said at least one diagnostic element wherein said deformable layer is capable of being deformed a distance whereby at least part of said porous material is brought into contact with said fluid delivery means.

7. A diagnostic device as defined in claim 1 wherein said porous material comprises a woven mesh material.

8. A diagnostic device as defined in claim 7 wherein said woven mesh material is a polymeric material.

* * * * *